United States Patent [19]

Kusakabe et al.

[11] Patent Number: 4,623,626
[45] Date of Patent: Nov. 18, 1986

[54] L-GLUTAMIC ACID OXIDASE AND ITS PRODUCTION

[75] Inventors: Hitoshi Kusakabe; Yuichiro Midorikawa, both of Choshi, Japan

[73] Assignee: Yamasa Shoyu Kabushiki Kaisha, Chiba, Japan

[21] Appl. No.: 509,226

[22] Filed: Jun. 28, 1983

[30] Foreign Application Priority Data

Jun. 29, 1982 [JP] Japan .................................. 57-112271

[51] Int. Cl.$^4$ .......................... C12Q 1/26; C12N 9/06; C12R 1/465
[52] U.S. Cl. ..................................... 435/191; 435/886
[58] Field of Search ................................... 435/25, 191

[56] References Cited

FOREIGN PATENT DOCUMENTS 57-43685 3/1982 Japan ..................................... 435/191

Primary Examiner—Lionel M. Shapiro
Attorney, Agent, or Firm—Wenderoth, Lind & Ponack

[57] ABSTRACT

L-glutamic acid oxidase, which is an L-amino acid oxidase catalyzing the oxidative deamination of the α-amino group of L-glutamic acid in the presence of water and oxygen to form α-ketoglutaric acid, ammonia and hydrogen peroxide, and having a very high substrate specificity for L-glutamic acid substantially without acting on L-glutamine and L-histidine, and also having a high stability, and a microbiological method of production thereof.

3 Claims, 7 Drawing Figures

L-GLUTAMIC ACID OXIDASE AND ITS PRODUCTION

BACKGROUND OF THE INVENTION

Field of the Invention

This invention relates to a novel L-glutamic acid oxidase and its production.

More specifically, the present invention relates to an L-glutamic acid oxidase which exhibits a strong affinity and a high substrate specificity for L-glutamic acid, but has substantially no action on other amino acids and yet has a high stability, and to a microbiological method of production thereof.

Recently, an L-amino acid oxidase having a substrate specificity for L-glutamic acid has been found to be produced by cultivation of a microorganism belonging to the genus Streptomyces (hereinafter sometimes abbreviated as "S."), more specifically *Streptomyces violascens* (See Japanese Patent Laid-Open Publication No. 43685/1982). The physicochemical properties of the glutamic acid oxidase (hereinafter sometimes abbreviated as "known enzyme") as a protein have not yet been clarified, but the known enzyme is described to have enzymological properties as follows.

(1) Substrate specificity

When the velocity of enzymatic reaction for L-glutamic acid is given as 100, the known enzyme has a relative activity of 8.4 for L-glutamine and 6.8 for L-histidine, exhibiting substantially no activity for other amino acids.

(2) Optimum pH pH 5-6

(3) pH stability

Stable in the range of pH 3.5–6.5 (37° C., maintained for one hour)

(4) Temperature stability

Stable up to 50° C. (maintained for 10 minutes)

(5) Influence of inhibitors

Substantially completely inhibited by mercury ions, copper ions and diethyldithiocarbamate.

The specification of the above Laid-Open Publication states that a liquid culture of the aforesaid microorganism is preferable for production of the known enzyme.

For utilization of the known enzyme for analysis of L-glutamic acid, various problems are involved. Specifically, although the known enzyme has a higher substrate specificity for L-glutamic acid as compared with other L-amino acid oxidases known in the art, it still exhibits clear activities for other amino acids as mentioned above, and therefore it cannot be used for specific quantitative determination of L-glutamic acid in the presence of these amino acids. Also, the known enzyme does not have a high pH stability and heat stability, and it cannot be considered to always have a good storage stability and stability during use as a reagent for analysis. Further, when copper ions exist in a sample to be analyzed, the activity of the known enzyme is markedly inhibited, whereby analysis may be considered to become difficult. Furthermore, the pH of reaction solutions employed in various clinical biochemical diagnostic analysis, especially in analysis of the activity of enzymes in blood, is usually around neutral, while the known enzyme will completely lose its activity at a pH of 7.5 when treated at 37° C. for one hour. For this reason, it may be difficult to use the known enzyme in analysis around the neutral pH range.

SUMMARY OF THE INVENTION

We have made investigations concerning enzymes which can oxidatively deaminate L-amino acids among the cultured products of microorganisms, and as a result have found that there exists an L-amino acid oxidase having an extremely high substrate specificity for L-glutamic acid in the cultured product of an actinomycete newly isolated from a soil sample. We have isolated and purified the enzyme of the present invention as a single enzyme protein from such a cultured product of the microorganism to accomplish the present invention.

The present invention provides an L-glutamic acid oxidase which is an L-amino acid oxidase having the ability to oxidatively deaminate the α-amino group of L-glutamic acid in the presence of water and oxygen to form α-ketoglutaric acid, ammonia and hydrogen peroxide. This oxidase has an extremely high substrate specificity for L-glutamic acid substantially without acting on L-glutamine and L-histidine, and also a high stability.

Further, the present invention also provides a method of producing an L-glutatic acid oxidase, which comprises culturing a microorganism belonging to the genus Streptomyces and having an ability to produce the aforesaid L-glutamic acid oxidase on a medium capable of growing the microorganism, and collecting the L-glutamic acid oxidase from the cultured product.

The enzyme of the present invention acts specifically on L-glutamic acid substantially without action on other amino acids, and therefore it is suitable for quantitative determination of L-glutamic acid in a system containing many kinds of amino acids. Its specificity for L-glutamic acid is so high that no pretreatment whatsoever of the sample, such as fractionation of amino acids in the sample, is required in carrying out the analysis. For example, it can be used for simple, rapid and specific measurement of glutamic acid content in foods containing many kinds of amino acids such as soy sauce, extracts, liquid seasonings, etc., the glutamic acid content being an important index in quality evaluation, for process control or process analysis in such fields as glutamic acid fermentation and production of soy sauce, and for screening of glutamic acid producing microorganisms. Also, since activity assays of enzymes forming glutamic acid as the product such as glutaminase, glutamic acid-oxaloacetic acid transaminase (GOT), glutamic acid-pyruvic acid transaminase (GPT), and γ-glutamyl transpeptidase (γ-GTP) can easily be done by the use of the enzyme of the present invention, this enzyme is useful in clinical diagnosis or in the field of biochemistry.

The enzyme of the present invention also has an advantage in the assay of its enzyme activity since its enzymatic reaction is an oxidase reaction most widely practiced in clinical diagnosis or food analysis.

Further, the enzyme of the present invention has a high stability when compared with enzymes for analysis in general including known enzymes, and therefore it can be utilized as an enzyme electrode for a glutamic acid sensor. It can also be expected to be utilized as a labelling enzyme in enzyme immunoassay (see Japanese Patent Laid-Open Publication No. 37261/1982), and further, the reagent for analysis is stable in storage and use, resulting in general applicability and economical advantage.

DETAILED DESCRIPTION OF THE INVENTION

Figure 1:
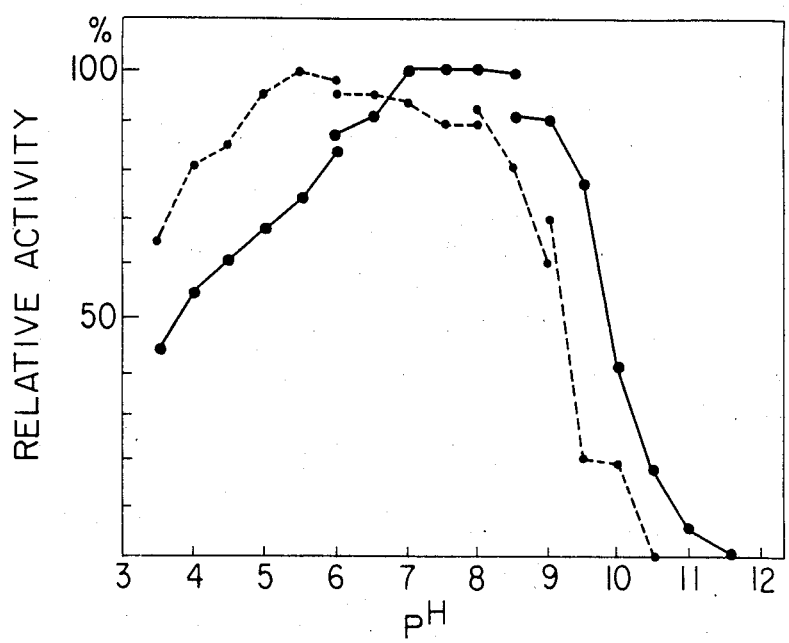
FIG. 1 is a graph showing active pH ranges of the enzyme of the present invention (solid line) and the known enzyme (broken line)

The enzyme of the present invention may be any L-glutamic acid oxidase which has a high stability and a very high substrate specificity for L-glutamic acid, substantially without action on amino acids other than L-glutamic acid, regardless of its preparation method.

An example of the enzyme of the present invention, is the enzyme obtained from the cultured product of a microorganism belonging to the genus Streptomyces, the properties and the method for preparation of this exemplary enzyme being detailed below.

(A) Enzymological and physicochemical properties of the enzyme of the present invention The purified enzyme sample of the L-glutamic acid oxidase prepared according to the method of the Example hereinafter described has enzymological and physicochemical properties as set forth below.

(1) Action:

The enzyme of the present invention, when employing L-glutamic acid as substrate, demands 1 mol of oxygen and 1 mol of water per 1 mol of L-glutamic acid, and forms 1 mol of α-ketoglutaric acid, 1 mol of ammonia and 1 mol of hydrogen peroxide, as shown in the following reaction scheme.

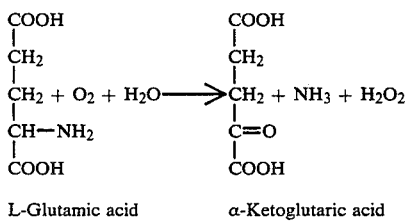

L-Glutamic acid     α-Ketoglutaric acid (2) Substrate specificity:

Table 1 shows the results obtained when the purified preparation of the enzyme of the present invention was caused to catalyze the oxidation of various amino acids. The concentration of each substrate was 10 mM, and the reactions were carried out at pH 7.4 (0.1 M potassium phosphate buffer) and pH 6.0 (0.1 M acetate buffer). The enzyme activities were measured according to the oxygen electrode method as hereinafter described, and expressed as the relative values of activities to L-glutamic acid.

TABLE 1

| Substrate | Relative Activity (%) pH 7.4 | pH 6.0 |
|---|---|---|
| L-Glutamic acid | 100.0 | 100.0 |
| D-Glutamic acid | <0.1 | <0.1 |
| L-Aspartic acid | 0.6 | <0.1 |
| L-Glutamine | <0.1 | <0.1 |
| L-Asparagine | <0.1 | <0.1 |
| Glycine | <0.1 | <0.1 |
| L-Alanine | <0.1 | <0.1 |
| L-Valine | <0.1 | <0.1 |
| L-Leucine | <0.1 | <0.1 |
| L-Isoleucine | <0.1 | <0.1 |
| L-Serine | <0.1 | <0.1 |
| L-Threonine | <0.1 | <0.1 |
| L-Phenylalanine | <0.1 | <0.1 |
| L-Tyrosine | <0.1 | <0.1 |
| L-Proline | <0.1 | <0.1 |
| L-Lysine | <0.1 | <0.1 |
| L-Ornithine | <0.1 | <0.1 |
| L-Histidine | <0.1 | <0.1 |
| L-Arginine | <0.1 | <0.1 |
| L-Cysteine | <0.1 | <0.1 |
| L Methionine | <0.1 | <0.1 |

As described above, the enzyme of the present invention has a high substrate specificity for L-glutamic acid. For other amino acids, it exhibits only a little activity (0.6%) for L-aspartic acid at pH 7.4, exhibiting substantially no activity for other L-amino acids including L-glutamine and L-histidine, or for D-glutamic acid. It also exhibits substantially no activity even for L-aspartic acid at pH 6.0.

As contrasted to the enzyme of the present invention, the known enzyme as described above exhibits no activity for L-aspartic acid (0.1% or less), but exhibits activities of 8.4% for L-glutamine and 6.8% for L-histidine, respectively. Thus, both enzymes are different from each other in substrate specificity.

The enzyme of the present invention has a km value for L-glutamic acid of $2.1 \times 10^{-4}$ M at pH 7.4, and a km value for L-aspartic acid of $2.9 \times 10^{-2}$ M at pH 7.4.

(3) Assay of activity:

The activity of the enzyme of the present invention was assayed according to the oxygen electrode method. That is, 1 ml of 0.1 M potassium phosphate buffer (pH 7.4) containing 10 mM sodium L-glutamate was charged into an oxygen electrode cell and 10 μl of an enzyme solution was added thereto to measure the oxygen consumption rate. One unit of enzyme was determined as the amount of enzyme which consumes 1μ mol of oxygen per minute at 30° C. in the absence of catalase (unit: hereinafter abbreviated as "U").

Since the dissolved oxygen concentration is reduced with elevation of the temperature, the above method cannot be used for activity assay at higher reaction temperatures. In such a case, the activity assay is conducted according to the MBTH method [Anal. Biochem., 25, 228 (1968)]. That is, a reaction mixture containing sodium L-glutamate, catalase and the enzyme of the present invention is incubated at an appropriate temperature for 20 minutes and the reaction is terminated with addition of trichloroacetic acid (TCA). To the terminated reaction mixture are added an acetate buffer (pH 5.0) and 3-methyl-2-benzothiazolinonehydrazone hydrochloride (MBTH) for incubation at 50° C. for 30 minutes, followed by cooling to room temperature, and thereafter the absorbance at 316 nm is measured to determine quantitatively the α-ketoglutaric acid formed from a calibration curve.

(4) Optimum pH:

The optimum pH is around pH 7 to 8.5 as shown in FIG. 1. The enzyme activities at respective pH values were assayed at 30° C. by using sodium L-glutamate as a substrate in 0.2 M acetate buffer (pH 3.5–6.0), 0.2 M potassium phosphate buffer (pH 6.0–8.5) and 0.2 M glycine-sodium chloride-sodium hydroxide buffer (pH 8.5–12.0).

In FIG. 1, for the purpose of comparison with respect to the optimum pH between the enzyme of the present invention and the known enzyme, both of the pH activity curves of the enzyme of the present invention (solid line) and the known enzyme (broken line: reference is made to FIG. 1 in Japanese Patent Laid-Open Publication No. 43685/1982) are shown.

As is apparent from FIG. 1, the enzyme of the present invention is different from the known enzyme also in the optimum pH.

Also, when employing aspartic acid as the substrate, the acting pH range is narrow, the optimum pH being 7 to 8, and the enzyme has substantially no action on L-aspartic acid at pH of 6.0 or less or at pH 10.0 or more (at pH 6.0, 0.1% or less of the relative activity for glutamic acid).

(5) pH stability:

After maintaining the enzyme at respective pH values of from pH 3.5 to 11.5, under the conditions of 37° C. for 60 minutes, 45° C. for 15 minutes and 60° C. for 15 minutes, the enzyme activity for glutamic acid was assayed at pH 7.4.

Figure 3:
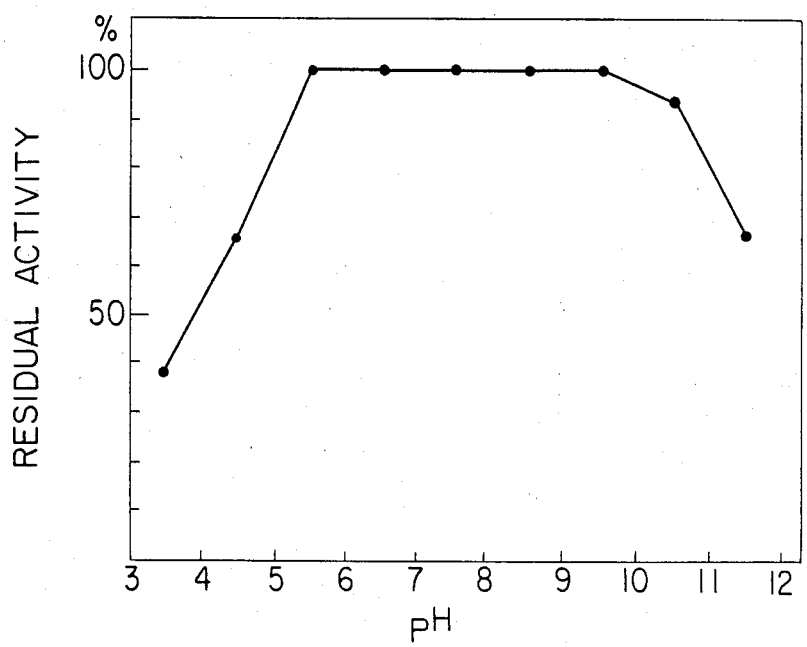
FIG. 3 is a graph showing the stable pH range (45° C., maintained for 15 minutes) of the enzyme of the present invention.
Figure 4:
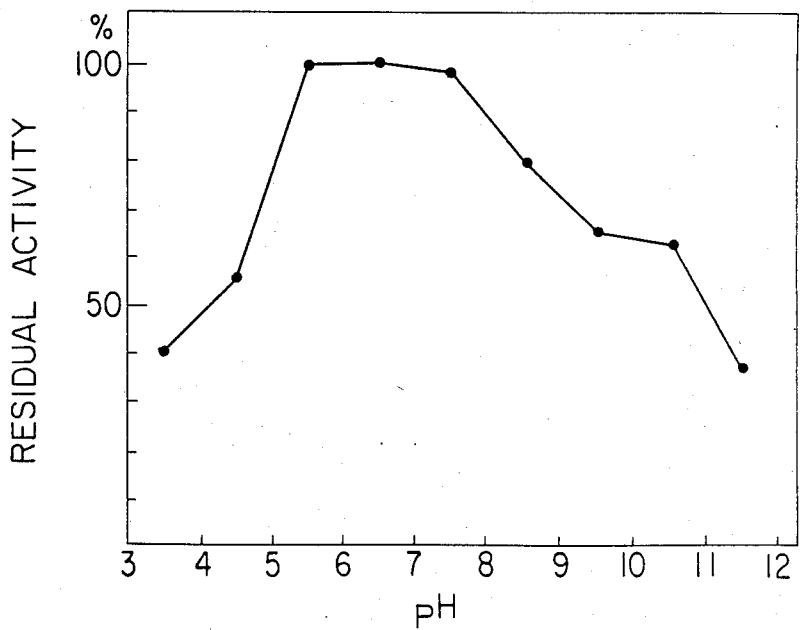
FIG. 4 is a graph showing the stable pH range (60° C., maintained for 15 minutes) of the enzyme of the present invention.

As a result, under the conditions of 37° C. for 60 minutes, the enzyme was stable at a pH range from 5.5 to 10.5 (FIG. 2, solid line); stable at a pH range from 5.5 to 9.5 under the conditions of 45° C. for 15 minutes (FIG. 3); and stable at a pH range from 5.5 to 7.5 under the conditions of 60° C. for 15 minutes (FIG. 4).

Figure 2:
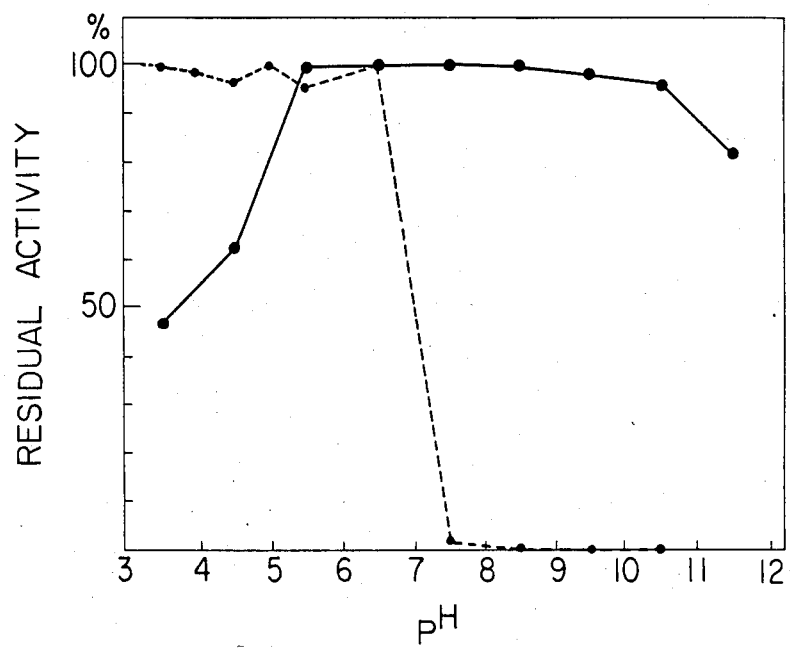
FIG. 2 is a graph showing stable pH ranges (37° C., maintained for 60 minutes) of the enzyme of the present invention (solid line) and the known enzyme (broken line)

In FIG. 2, for the purpose of comparison relative to pH stability between the enzyme of the present invention and the known enzyme, both of the pH stability curves of the known enzyme (broken line: reference is made to FIG. 2 in Japanese Patent Laid-Open Publication No. 43685/1982) and the enzyme of the present invention are shown.

As is apparent from FIGS. 2, 3 and 4, when stable pH ranges are compared between the enzyme of the present invention and the known enzyme, both are clearly different from each other, the former being stable at a wider pH range as compared with the latter.

(6) Suitable acting temperature range:

At respective temperatures of 30° C. to 80° C., the reactions were carried out for 20 minutes with the use of sodium L-glutamate as a substrate, and the enzyme activity was assayed according to the MBTH method as described above.

Figure 5:
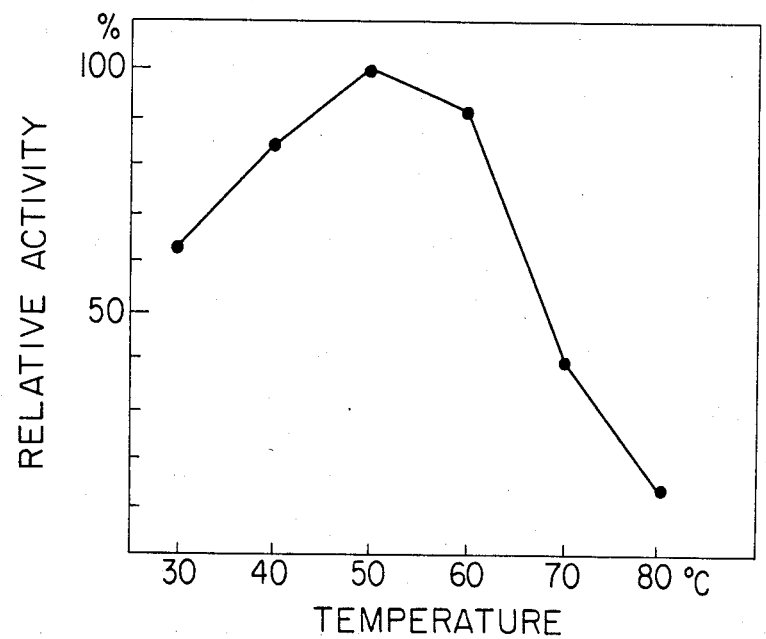
FIG. 5 is a graph showing the optimum acting temperature range of the enzyme of the present invention.

As a result, the suitable acting temperature range of the enzyme of the present invention was found to be 30° to 60° C., with the optimum acting temperature being around 50° C. (FIG. 5).

(7) Thermal stability:

After maintaining the enzyme at respective temperatures of 40° C. to 90° C. under the respective conditions of pH 5.5, pH 7.5 and pH 9.5, for 15 minutes, the enzyme activity for glutamic acid was assayed at pH 7.4.

Figure 6:
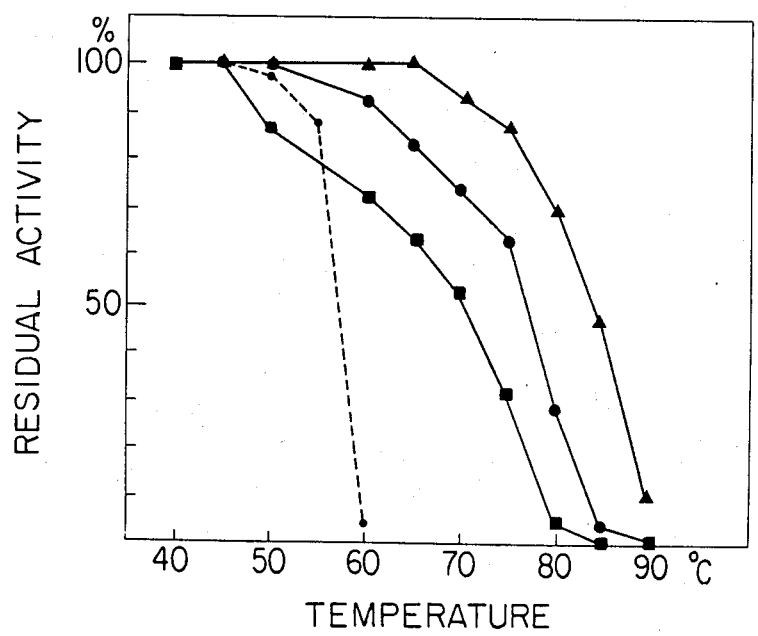
FIG. 6 is a graph showing stable temperature ranges of the enzyme of the present invention for different pH values (solid line), and the known enzyme (broken line)

As a result, the enzyme was found at pH 5.5 to be stable up to 65° C., exhibiting a residual activity of about 50% at 85° C. (FIG. 6, ▮ - ▮). At pH 7.5, it was stable up to 50° C., exhibiting a residual activity of about 60% at 75° C. (FIG. 6, ● - ●). At pH 9.5, it was stable up to 45° C., exhibiting a residual activity of about 50% at 70° C. (FIG. 6, ■ - ■).

For the purpose of comparison with regard to thermal stability between the enzyme of the present invention and the known enzyme, the temperature stability curve of the known enzyme (broken line: reference is made to FIG. 3 in Japanese Patent Laid-Open Publication No. 43685/1982) and that of the enzyme of the present invention are shown in the same drawing.

As is apparent from FIG. 6, the enzyme of the present invention has a higher thermal stability than the known enzyme.

(8) Inhibition, Activation and Stabilization:

For examination of the effects of various additives on the enzyme activity of the present invention, enzymatic reaction was carried out in a reaction mixture (pH 7.4) containing each of the substances shown in Table 2 at a concentration of 1 mM.

The results are as shown in Table 2.

TABLE 2

| Additives | Relative activity | Additives | Relative activity |
|---|---|---|---|
| (No addition) | 100 | $MnSO_4$ | 102.1 |
| KCl | 111.1 | $CoSO_4$ | 100.7 |
| NaCl | 95.8 | $Al_2(SO_4)_3$ | 93.8 |
| KI | 100.7 | EDTA[1] | 96.5 |
| NaF | 107.6 | NEM[2] | 94.4 |
| $CaCl_2$ | 100.0 | PCMB[3] | 55.6 |
| $CuCl_2$ | 100.7 | o-phenanthroline | 97.8 |
| $BaCl_2$ | 95.1 | α, α'-dipyridyl | 94.4 |
| $NiCl_2$ | 96.5 | $NaN_3$ | 100.6 |
| $StCl_2$ | 97.2 | DDTC[4] | 100.7 |
| $Li_2SO_4$ | 93.8 | Tiron[5] (trade mark) | 100.7 |
| $ZnSO_4$ | 90.3 | | |

[1]EDTA: ethylenediaminetetraacetic acid
[2]NEM: N—ethylmaleimide
[3]PCMB: p-chloromercuribenzoate
[4]DDTC: diethyldithiocarbamate
[5]Tiron: 4,5-dihydroxy-1,3-benzenedisulfonic acid disodium salt As is apparent from Table 2, the activity of the enzyme of the present invention is inhibited by about 45% by p-chloromercuribenzoate but is not inhibited at all by cupric chloride and diethyldithiocarbamate. On the other hand, the activity of the known enzyme is completely inhibited by cupric chloride and diethyldithiocarbamate. Therefore, both of the enzymes are different from each other also with respect to the effect by inhibitors.

At present, no activator and stabilizer have been found for the enzyme of the present invention.

Figure 7:
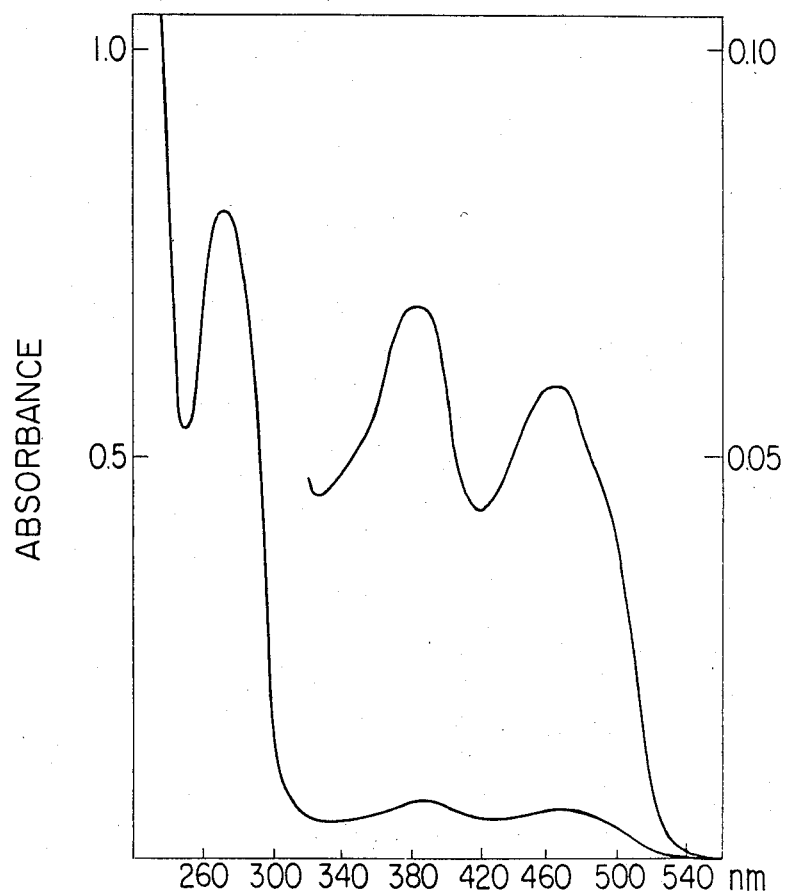
FIG. 7 is a graph showing the UV-absorption spectrum of the enzyme of the present invention.

(9) UV-absorption spectrum (see FIG. 7):

$\lambda_{max}$: 273 nm, 385 nm, 465 nm.

Shoulder: around 290 nm, around 490 nm.

(10) Coenzyme:

The absorption spectrum of the supernatant obtained by heat treatment or trichloroacetic acid (TCA) treatment of the enzyme of the present invention was identical with that of flavin adenine dinucleotide (FAD). The supernatant activated the apoenzyme of D-amino acid oxidase, and therefore the coenzyme of the enzyme of the present invention was found to be FAD.

The yellow compound in the supernatant was also identified as FAD from the Rf value in thin layer chromatography.

FAD was estimated to exist in an amount of 2 mol per 1 mol of the enzyme of the present invention.

(11) Polyacrylamide gel electrophoresis:

The purified enzyme of the present invention exhibited a single band.

(12) Molecular weight:

The enzyme of the present invention was estimated to have a molecular weight of 135,000±10,000 according to the gel filtration method by the use of Sephadex G-200 (produced by Pharmacia Fine Chemicals, Inc.).

(13) Isoelectric point:

The isoelectric point was measured by electrophoresis by the use of Ampholine (produced by LKB Co.) to find that PI was 6.2.

(14) Crystalline structure and elemental analysis:

The enzyme of the present invention was not crystallized, and no measurement has been performed.

(15) Purification method:

The enzyme of the present invention can be purified according to procedures involving salting out, isoelectric point precipitation, precipitation by an organic solvent, adsorption with diatomaceous earth, activated charcoal, etc., various chromatographies, and others. Examples of the purification methods are shown in the Example.

(B) Preparation of the enzyme of the present invention

The method for producing the enzyme of the present invention will now be described in detail.

Microorqanism employed

The microorganism employed in the production of the enzyme of the present invention belongs to the genus of Streptomyces and is a microorganism capable of producing the enzyme of the present invention.

Illustrative of such a microorganism is the X-119-6 strain isolated as a single strain from a soil sample in Tōnoshō-machi, Katori-gun, Chiba-ken, Japan. The properties of this strain are described below.

A. Microscopic observation

Aerial mycelia are straight with widths of 0.9 to 1.0μ, exhibiting simple branching. Sporophores consist of a number of chains of spores, forming spirals of 2 to 5 rotations. Spores are somewhat ellipsoidal with sizes of 0.9-1.0×1.1×1.2μ, and the surface is observed by electron microscope to have a spiny structure. No breaking of the basal mycelia is observed.

B. Observation by naked eye

The results of observation by naked eye after growth on various media (30° C., 16 days' cultivation) are as follows.

(1) Sucrose-nitrate agar medium:

Its growth is poor. The basal mycelia are grayish brown and do not penetrate into the agar, and the aerial mycelia are powdery and spread radially on the agar. The aerial mycelia are grayish brown, with formation of gray spores. No formation of pigment into the medium is observed.

(2) Glucose-asparagine agar medium:

Its growth is good. The basal mycelia are white yellow, penetrate into the agar, and are also slightly raised. The aerial mycelia are white with no formation of pigment into the medium.

(3) Glycerin-asparagine agar medium:

Its growth is good. The basal mycelia are white yellow, penetrate into the agar, and are also raised. No aerial mycelium is formed, and no formation of pigment into the medium is observed.

(4) Starch-inorganic salts agar medium:

Its growth is good. The basal mycelia are white yellow, penetrate into the agar, and are also raised. The aerial mycelia are white and abundant with formation of gray spores. No pigment formation into the medium is observed.

(5) Tyrosine-agar medium:

Its growth is good. The basal mycelia are white yellow. The aerial mycelia are white and abundant with formation of gray spores. No pigment formation into the medium is observed.

(6) Nutrient-agar medium:

Its growth is very good. The basal mycelia are white yellow, penetrate into the agar, and are also raised. The aerial mycelia are white, with no formation of spore being observed. No pigment formation into the medium is observed.

(7) Yeast-malt agar medium:

Its growth is very good. The basal mycelia are white yellow, penetrate into the agar, and are also raised. The aerial mycelia are white and abundant with formation of gray spores. No pigment formation into the medium is observed.

(8) Oatmeal-agar medium:

Its growth is very good. The basal mycelia are white, penetrate into the agar, but are not raised on the medium. The aerial mycelia are white and abundant with formation of gray spores. No pigment formation into the medium is observed.

C. Physiological properties

Growth temperature range is 8° to 40° C., the optimum temperature being around 35° C.

In both of the tyrosine-agar medium and the peptone-yeast-iron-agar medium, no melanin-like pigment is formed; gelatin is slightly liquefied; and starch is hydrolyzed.

D. Assimilability of various carbon sources

Utilizations of various carbon sources on the Pridham-Gottrieb agar medium are as shown in Table 3.

TABLE 3

| Carbon source | Utilization* |
|---|---|
| D-Glucose | + |
| D-Xylose | − |
| L-Arabinose | + |
| L-Rhamnose | − |
| D-Fructose | + |
| Raffinose | + |
| Mannitol | + |
| Inositol | + |
| Sucrose | + |

*+: utilized, −: not utilized.

The above properties may be summarized as follows. That is, aerial mycelia are spiral, the surfaces of the spores being spiny. Growth on media exhibits white yellow color or grayish brown color, aerial mycelia being colored white to grayish brown, and no formation of soluble pigment and melanin-like pigment is observed. Furthermore, starch hydrolyzability is rather strong.

On the basis of these results and assimilability of carbon sources shown in Table 3, the present microorganism strain was classified according to the taxonomic system in Bergey's Manual of Determinative Bacteriology, eighth edition (1974), whereby it was found that the present microorganism strain belongs to the genus Streptomyces, but no known species sufficiently coinciding in characteristics with the present strain was found, and hence the present strain was identified to be a new microorganism strain and named Streptomyces sp. X-119-6.

The present microorganism strain was deposited at the Fermentation Research Institute, Agency of Industrial Science and Technology (FRI), 1-3, Higashi 1-chome, Yatabe-machi, Tsukuba-gun, Ibaraki-ken, Japan on June 5, 1982, and given the deposition number FERM P-6560. This strain was delivered directly from FRI to American Type Culture Collection, 12301 Parklawn Drive, Rockville, Md., U.S.A. and acquired the deposition number ATCC 39343 on April 26, 1983.

The above microorganism strain is one example of the microorganism strains having high capability of producing the enzyme of the present invention, and the microorganism to be used in the present invention is not limited thereto. It is also possible to suitably use any of the mutant strains highly capable of producing the enzyme of the present invention obtained by subjecting the microorganism producing the enzyme of the present invention to conventional microorganism mutating methods such as physical treatment by UV-ray, X-ray or γ-ray irradiation, chemical treatments with reagents such as nitrosoguanidine, etc. Further, the methods for the enzyme production are based on the function of the synthesis of the enzyme protein by the structure and regulator DNA gene in the aforesaid microorganism producing the enzyme of the present invention. Accordingly, also included within the scope of the present invention is the production method using a microorganism, which is obtained by gene manipulation procedure, for example, by incorporating such a gene DNA into an appropriate vector which is in turn transferred by way of transformation into a microorganism belonging to a genus other than the aforesaid genus, or by permitting the gene DNA to be taken up in an a microorganism belonging to the other genus by cell fusion according to the protoplast method.

Cultural method and conditions

The cultural method and conditions for cultivating the above microorganism to be used in the present invention are not particularly limited, as long as the microorganism can sufficiently grow and the enzyme of the present invention can be sufficiently produced, but it is preferred to use a solid cultivation method or similar method.

The solid medium to be used in solid cultivation is not different in any way from those conventionally used. That is, the solid medium is mainly composed of one or more kinds of natural solid materials such as wheat bran, defatted soy bean, rice bran, corn, rapeseed dregs, wheat, rice, rice hulls, etc., further containing, if desired, nutrient sources assimilable by the microorganism employed in the present invention, as exemplified by carbon sources such as glucose, sucrose, arabinose, fructose, mannitol, inositol, soluble starch, ethanol, etc., nitrogen sources such as various amino acids, peptone, soybean powders, protein hydrolysates, corn steep liquor, meat extract, yeast extract, various ammonium salts, various nitrates, urea, etc., growth promoters exemplified by salts such as various sodium salts, potassium salts, calcium salts, manganese salts, magnesium salts, zinc salts, iron salts, phosphates, sulfates, etc., and vitamins such as thiamine, riboflavin, nicotinic acid, pantothenic acid, biotin, p-aminobenzoic acid, cyanocobalamin, etc. These media may also be granulated in suitable formulations, sizes and shapes. Such a solid medium may be sterilized or denatured according to conventional procedures and then inoculated with a seed microorganism to carry out solid cultivation.

It is also possible to employ a cultivation method other than the above method, as long as the microorganism employed can proliferate and produce the enzyme of the present invention well, such as the method in which a liquid medium is absorbed into or coated over a suitable carrier such as sponge, etc. (see Japanese Patent Laid-Open Publication No. 14679/1974), and a seed microorganism is inoculated into the medium to be cultured therein.

The cultural conditions are not particularly limited and may be selected for optimal production of the enzyme depending on the kind of the microorganism employed. Generally, cultivation may be conducted under the conditions of, for example, 20°-30° C., pH 5-7 and 5-15 days.

Collection of the enzyme of the present invention

The enzyme of the present invention produced by cultivation of the microorganism employed may be separated by extraction from the cultured product, namely, the medium and/or the cultured microorganism cells, according to a suitable extraction method. The enzyme may be used as the crude enzyme solution or purified according to a conventional enzyme purification method to a purification degree which depends on the purpose of use.

The extraction method is not particularly limited but may be a conventional method. For example, extraction from the solid cultured product is ordinarily conducted with water or a buffer. The enzyme of the present invention in microorganism cells is extracted after crushing the microorganism cells in a conventional manner and solubilizing the enzyme.

In order to indicate more fully the nature of the present invention, the following specific example of practice constituting a preferred embdiment of the invention is set forth, it being understood that this example is presented as illustrative only and is not intended to limit the scope of the invention.

Example

Into an Erlenmeyer flask of 500-ml capacity were charged 20 g of wheat bran and 16 ml of water, and the sterilization was conducted at 120° C. for 30 minutes. Into the wheat bran medium thus prepared, Streptomyces sp. X-119-6 (FERM P-6560, ATCC 39343) was inoculated and cultured at 28° C. for 7 days to prepare seed culture.

Into each of 25 Erlenmeyer flasks of 5-liter capacity were charged 200 g of wheat bran and 160 ml of water, and after sterilization at 120° C. for 30 minutes, the above seed culture was inoculated and cultured at 28° C. for 2 days and further at 20° C. for an additional 2 weeks.

The cultured product obtained was immersed in 37.5 liters of water for one hour, filtered and further passed through diatomaceous earth to obtain about 34 liters of a crude enzyme solution. Ammonium sulfate was added to the crude enzyme solution to 50% saturation, and the precipitates formed were collected by centrifugation and dissolved in 3.9 liters of 0.02 M acetate buffer (pH 5.5). The resultant solution was heated at 57° C. for 30 minutes. The heat treated enzyme solution was cooled to 5° C. or lower, and then to this solution was added a two-fold amount of previously cooled ethanol. The precipitates thus formed were collected by centrifugation, dissolved in 0.02 M phosphate buffer (pH 7.4), and dialyzed against the same buffer overnight.

The precipitates formed during dialysis were removed by centrifugation. The supernatant was passed through a DEAE (diethylaminoethyl) - cellulose column (3.5×50 cm) equilibrated with the same buffer, and the enzyme adsorbed was eluted with the same buffer containing 0.35 M sodium chloride. The active fractions eluted were collected, and dialyzed against 0.05 M acetate buffer (pH 5.5) containing 0.05 M sodium chloride. The inner dialyzed solution was passed through a column (2×10 cm) of DEAE-Sepharose CL-6B (produced by Pharmacia Fine Chemicals, Inc.) equilibrated with the same buffer, and the enzyme adsorbed was eluted with 0.05–0.75 M linear gradient of sodium chloride.

The active fractions eluted were collected, concentrated by dialysis, and then subjected to gel filtration by use of a Sephadex G-200 (produced by Pharmacia Fine Chemicals, Inc.) column (2.5×120 cm). The active fractions were collected and, after concentration, dialyzed against 0.02 M potassium phosphate buffer (pH 7.4). The inner dialyzed solution was centrifuged, and the supernatant was subjected to microfiltration, which was followed by lyophilization to obtain 30 mg of a purified preparation of L-glutamic acid oxidase (specific activity 55.1 U/mg-protein, yield 18.4%).

What is claimed is:

1. An L-glutamic acid oxidase which is an L-amino acid oxidase having activity of oxidative deamination of the α-amino group of L-glutamic acid in the presence of water and oxygen to form α-ketoglutaric acid, ammonia and hydrogen peroxide; having a substrate specificity for L-glutamic acid substantially without acting on L-glutamine and L-histidine; and having the following properties:
   (a) stable in the pH range from 5.5 to 10.5 under maintenance conditions of 37° C. and 60 minutes;
   (b) stable in the temperature range of up to 65° C. under maintenance conditions of pH 5.5 and 15 minutes;
   (c) optimum activity in the pH range from 7 to 8.5;
   (d) is not inactivated by cupric chloride in a concentration of 1.0 mM at pH 7.4;
   (e) contains 2 mols of flavin adenine dinucleotide per mol of the oxidase as a coenzyme; and
   (f) a molecular weight of 135,000±10,000 as estimated by gel filtration.

2. A method of producing the L-glutamic acid oxidase of claim 1, which comprises culturing Streptomyces sp. X-119-6 or a microorganism derived therefrom having an ability to produce the L-glutamic acid oxidase on a medium capable of growing said Streptomyces on the microorganism derived therefrom and collecting said L-glutamic acid oxidase from the cultured product.

3. A method according to claim 2, wherein said microorganism is Streptomyces sp. X-119-6.

* * * * *